United States Patent [19]
Duarte

[11] Patent Number: 5,958,336
[45] Date of Patent: Sep. 28, 1999

[54] SURFACE STERILIZATION DEVICE

[76] Inventor: Raul Duarte, 1 Eleventh Fairway Ct., Belleville, Ill. 62220

[21] Appl. No.: 08/638,144

[22] Filed: Apr. 26, 1996

[51] Int. Cl.$^6$ ............................... A61L 2/08; A61L 2/10; A61L 2/00
[52] U.S. Cl. ............................. 422/24; 422/25; 422/121; 422/186.3; 250/453.11; 250/454.11; 250/455.11
[58] Field of Search ................................ 422/24, 25, 121, 422/186.3; 250/453.11, 454.11, 455.11

[56] References Cited

U.S. PATENT DOCUMENTS

| | | | |
|---|---|---|---|
| 2,935,156 | 5/1960 | Scofield . | |
| 3,623,903 | 11/1971 | Dislich et al. | 385/145 |
| 3,671,380 | 6/1972 | Ali et al. | 385/144 |
| 3,994,073 | 11/1976 | Lackore | 34/277 |
| 4,003,714 | 1/1977 | Foglino et al. | 422/307 |
| 4,140,479 | 2/1979 | Sirch et al. | 432/18 |
| 4,175,140 | 11/1979 | Bachmann et al. | 426/399 |
| 4,289,728 | 9/1981 | Peel et al. | 422/24 |
| 4,309,388 | 1/1982 | Tenney et al. | 422/304 |
| 4,366,125 | 12/1982 | Kodera et al. | 422/295 |
| 4,385,035 | 5/1983 | Akitoshi et al. | 422/297 |
| 4,504,114 | 3/1985 | Arrington | 385/142 |
| 4,682,927 | 7/1987 | Southworth et al. | 414/217 |
| 4,821,866 | 4/1989 | Melgaard | 198/494 |
| 4,877,964 | 10/1989 | Tanaka et al. | 250/455.11 |
| 4,944,132 | 7/1990 | Carlsson et al. | 53/167 |
| 4,981,650 | 1/1991 | Brown et al. | 422/24 |
| 5,064,614 | 11/1991 | Reiss et al. | 422/22 |
| 5,069,017 | 12/1991 | Fabricius | 53/426 |
| 5,114,670 | 5/1992 | Duffey | 422/24 |
| 5,115,136 | 5/1992 | Tomasch | 250/461.1 |
| 5,258,162 | 11/1993 | Andersson et al. | 422/28 |
| 5,326,542 | 7/1994 | Sizer et al. | 422/291 |
| 5,350,568 | 9/1994 | Tuckner et al. | 422/300 |
| 5,368,815 | 11/1994 | Kasting, Jr. et al. | 422/3 |
| 5,368,828 | 11/1994 | Carlson | 422/300 |
| 5,377,475 | 1/1995 | Haarer et al. | 53/167 |
| 5,385,677 | 1/1995 | Venable | 210/748 |
| 5,446,289 | 8/1995 | Shodeen et al. | 250/455.11 |
| 5,597,597 | 1/1997 | Newman | 426/248 |
| 5,673,535 | 10/1997 | Jagger | 53/282 |

OTHER PUBLICATIONS

Melgaard, Hans L., "The Use of Ultraviolet Energy to Disinfect/Sterilize Surfaces in a Continuous Mode," International Society for Pharmaceutical Engineering, Barrier Isolation Technology Conference, Rockville, Maryland, Dec. 4–6, 1995.
Davenport, Stewart M. and Hans L. Melgaard, "Ultraviolet Pass–Through as a Transfer Technology in Barrier and Isolator Systems," Atlanta Conference, Jan. 1995.
Product Catalog, "UV Process Supply, Inc.," UV Process Supply, Inc., Chicago, IL, Copyright, 1994.
Specification, "Super II Econoflo," Clestra Cleanroom Components, Issued Nov. 13, 1992.
Catalog, "Germicidal Lamps," General Electric, 1987.

*Primary Examiner*—Lila Feisee
*Assistant Examiner*—Michael Pak
*Attorney, Agent, or Firm*—Blackwell Sanders Peper Martin

[57] ABSTRACT

A device for surface sterilization of objects includes a housing, a conveyor assembly including a frame, a conveyor bed selectively movably connected to the frame and a plurality of legs spacedly disposed beneath and supporting the frame above a support surface. At least part of the conveyor bed is located longitudinally within the housing to thereby movably support objects to be surface sterilized as they are passed through the housing from a contaminated area to a clean area. An air filtration system is in communication with the housing, and at least one ultraviolet light assembly is located within of the housing to decontaminate the object to be surface sterilized within the sterilization device as the object is transferred via the conveyor through the housing and into the clean area.

28 Claims, 10 Drawing Sheets

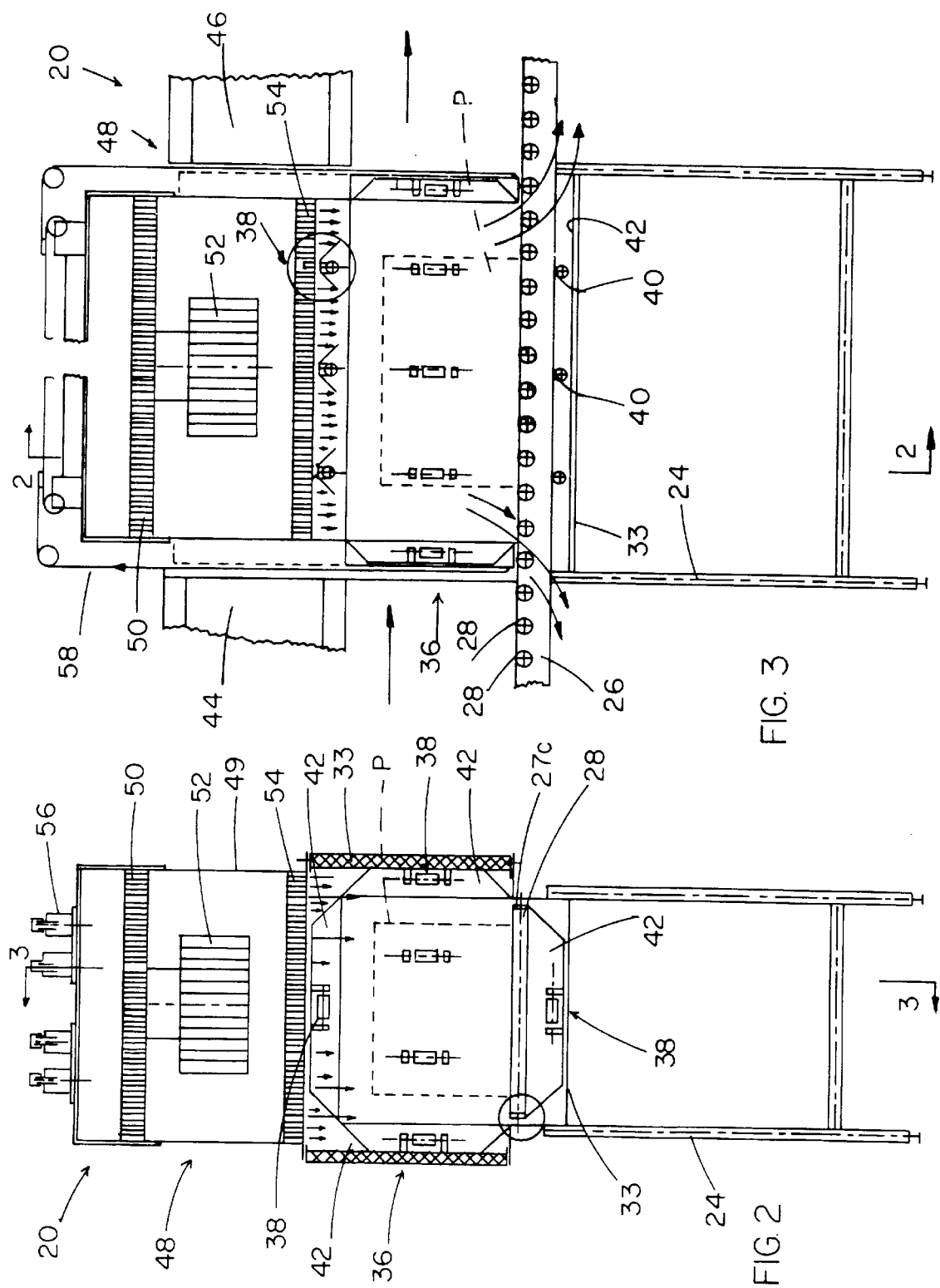

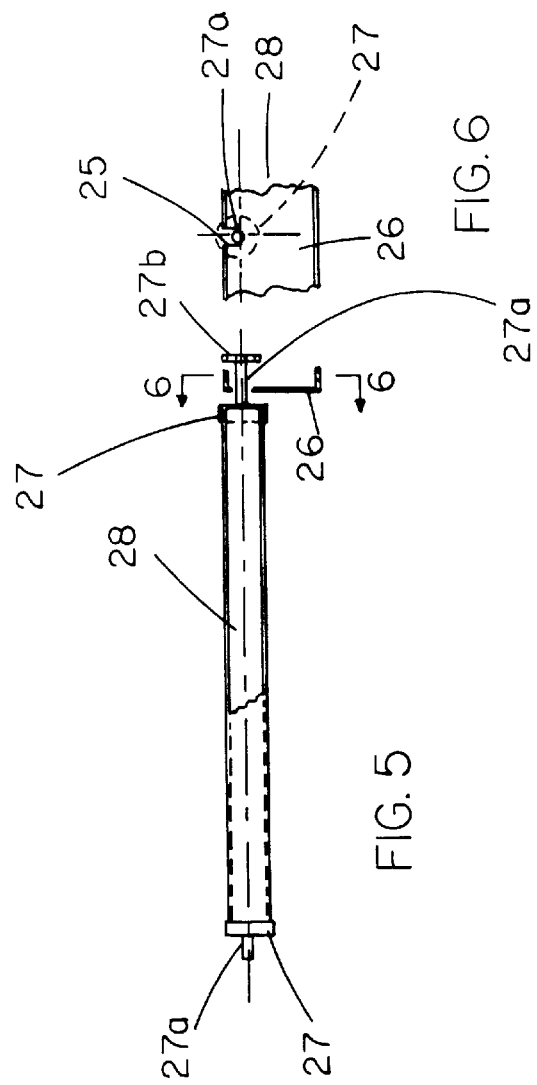
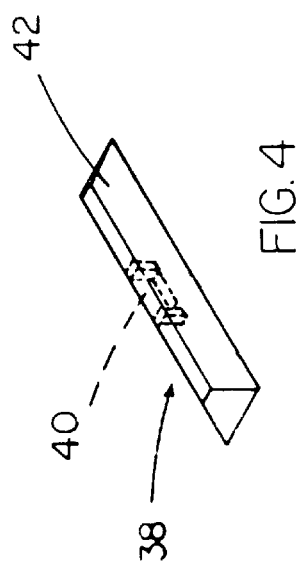

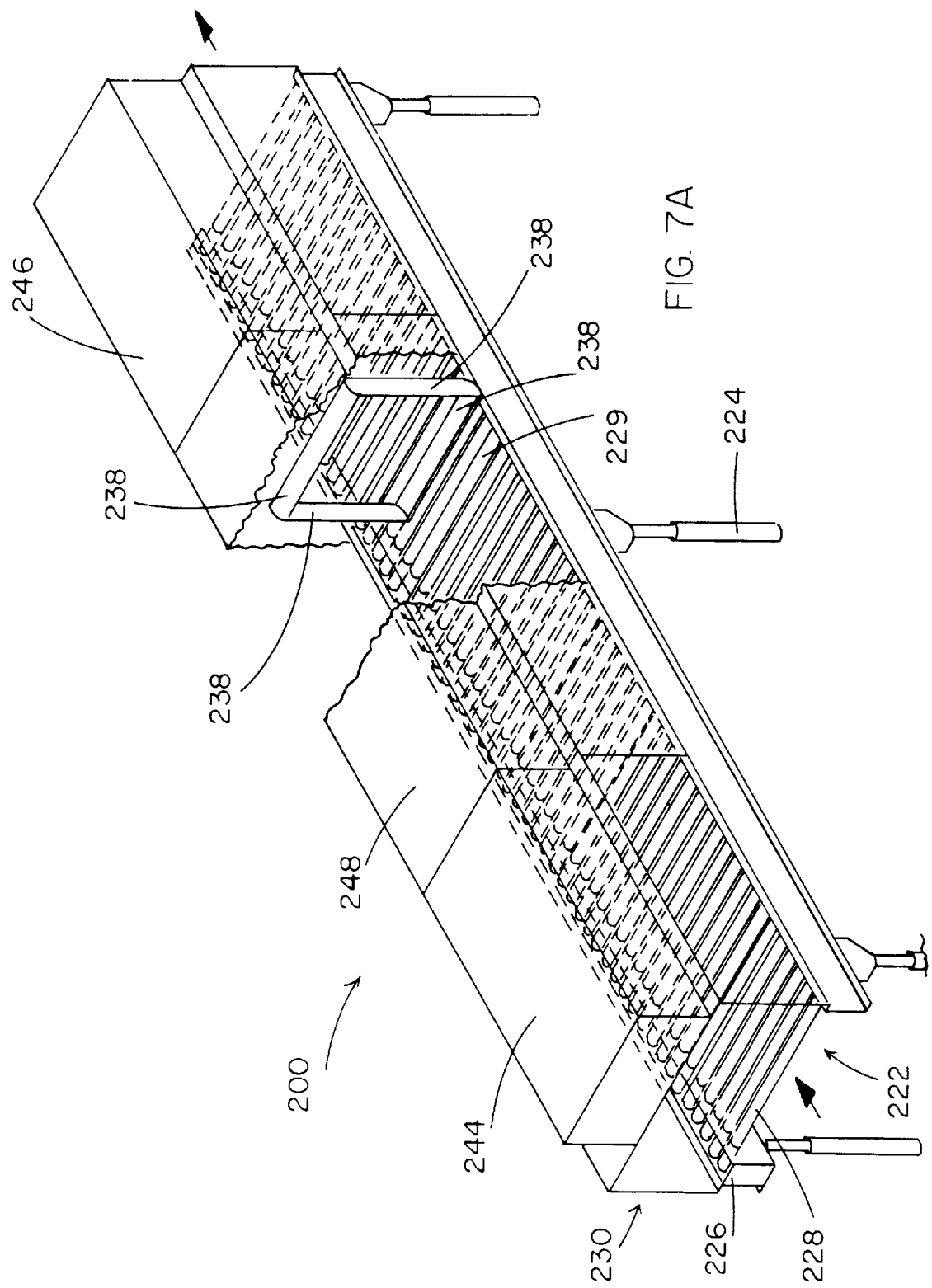

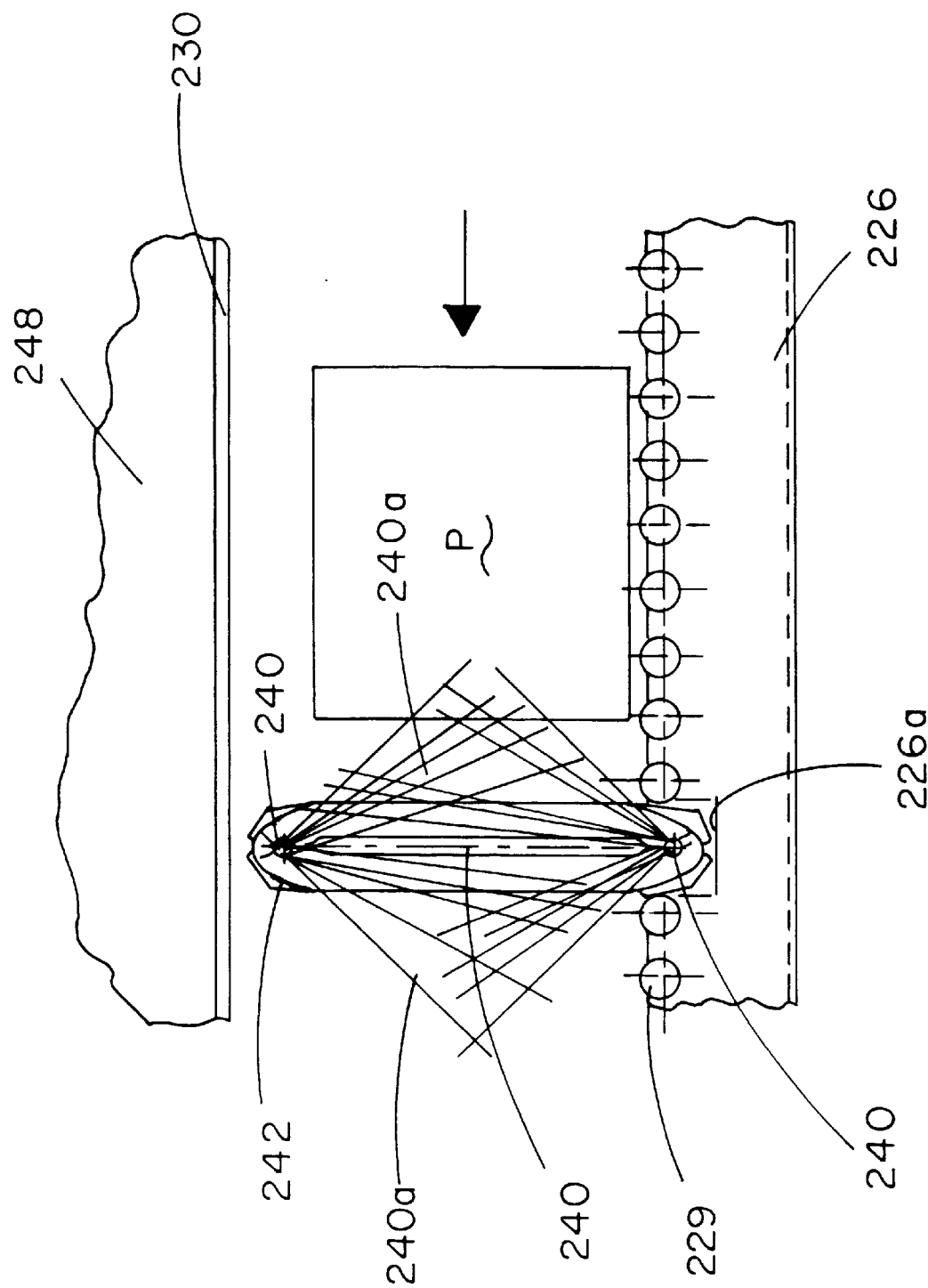

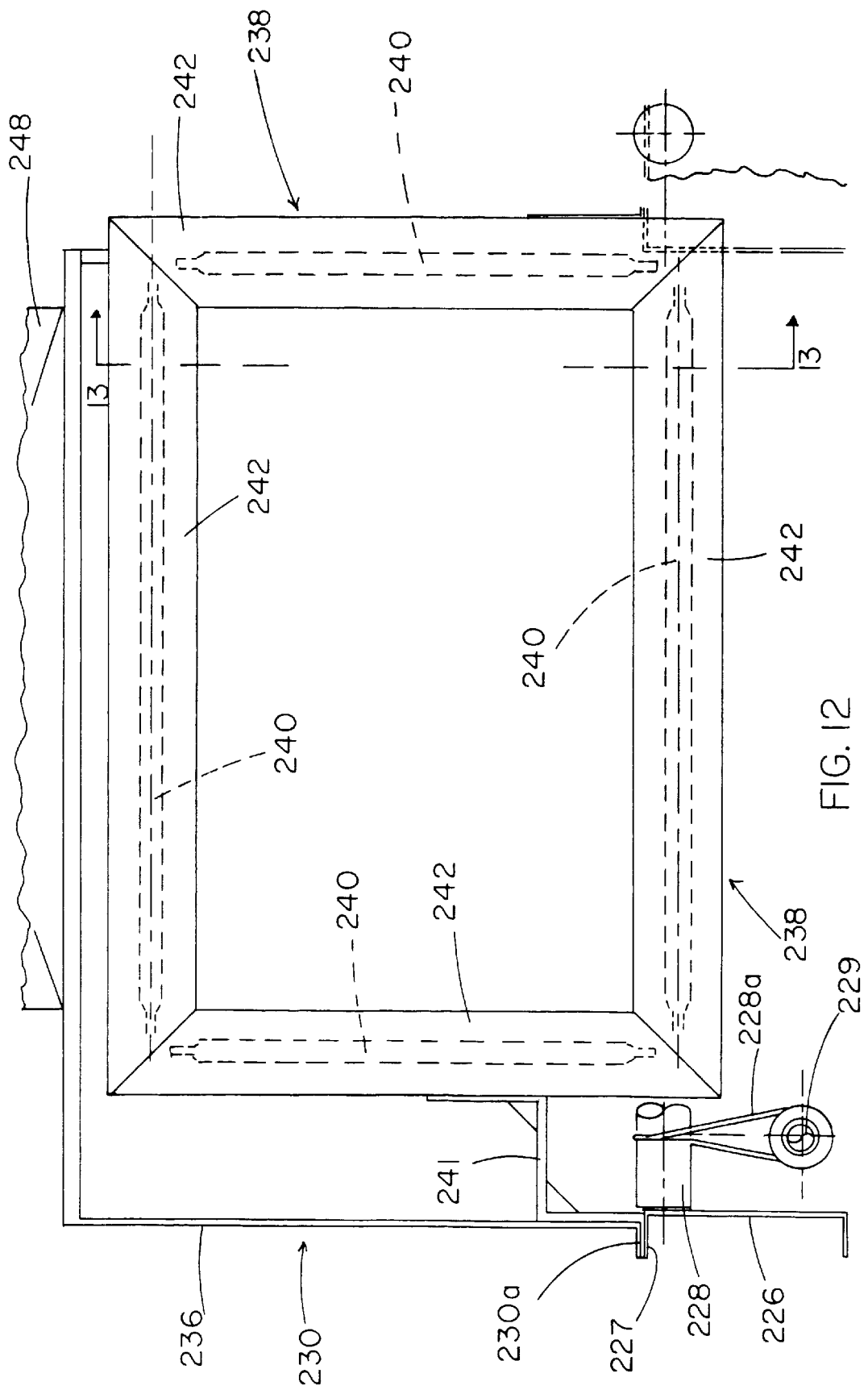

SURFACE STERILIZATION DEVICE

BACKGROUND AND SUMMARY OF THE INVENTION

The present invention relates generally to the field of sterilization equipment, and, more specifically, to a device for surface sterilization of objects of various regular or irregular shapes, which device includes the combination of ultraviolet lamps, HEPA air filters and a pass-through sterilization chamber within a tunnel-like housing which covers a conveyor.

Previously, the pharmaceutical industry used glass bottles for the purpose of filling liquids and powder in a sterile manner in rooms which meet specific standards, referred to in the industry as "Class 100," for levels of cleanliness and sterility. The three traditional sterilization methods used are as follows: 1.) the glass bottles are passed into the clean room by sterilizing batches of bottles in a double door autoclave, loading the bottles on the "dirty" side of the autoclave, and, after sterilizing, opening the autoclave door on the clean room side, allowing the sterile bottles to be passed through the autoclave into the clean room for filling with sterile liquid; 2.) sterilizing batches of bottles in a double door hot air oven, loading the bottles on the dirty side, and as with the autoclave in number 1., after the bottles are sterilized, the oven door inside the clean room is opened, allowing the sterile bottles to be passed through manually into the clean room for filling; and 3.) using a hot air sterilizing tunnel to decontaminate the bottles, loading the bottles on the dirty side and automatically discharging them into the clean room for filling.

Although the above methods were satisfactory for sterilizing glass bottles, they cannot be used for bottles produced of the plastics now available, because all of these methods will cause the plastic bottles to melt during the sterilization process, rendering the bottles completely useless. Thus, at present, plastic bottles for filling with sterile liquids and powders are now filled and closed in what is commonly referred to in the industry as "Class 100" or "clean" rooms.

The currently used plastic bottles for sterile filling are manufactured in such clean rooms, and packaged into cardboard trays before shrink-wrapping and then exposed to gamma radiation for sterilization of the inside of the bottles. The sterile, shrink-wrapped trays of bottles are then shipped in plastic bags to customers for filling with the desired sterile substance.

The difficulty arises when a customer receives the wrapped, sterile plastic bottles. The problem lies in how to introduce the contaminated exterior bags containing the bottles into the clean room without breaking sterility of the room. Some attempts have been made to work with generators of hydrogen peroxide vapors. One example of this approach is such a vapor generator developed and currently marketed by AMSCO Scientific, a Division of American Sterilizer Co. Although with the AMSCO device hydrogen peroxide decontaminates the outer surface of the containment bag; at the same time, the vapor permeates through the plastic bag, contaminating the inside of the shrink-wrapped bottles with free radicals of hydrogen and oxygen, which may be highly undesirable in contact with the particular sterile substance to be introduced into the sterile plastic bottles.

Other disadvantages with the hydrogen peroxide vapor method are that a relative humidity of approximately 40% is necessary for vaporization, and health hazards are posed by the high levels of hydrogen peroxide vapor. Furthermore, this system requires a long period of time for the cycle of decontamination, including vapor generation and evacuation of the vapor from the package being sterilized.

Another known approach to the above described problem has been to simply place the plastic bag filled with previously sterilized bottles under a HEPA filter module pass-through unit in hopes of decontaminating the outside sufficiently that the clean room into which the bag is introduced does not break the sterile environment. Unfortunately, particularly with articles of irregular shape, such as large, loosely packed plastic bags, decontamination can be incomplete due to contaminants becoming trapped in folds and crevices of the exterior package.

Similar short-comings exist with previous uses of ultraviolet ("U.V.") or other germicidal lights, in that all surfaces of the package to be decontaminated are not necessarily accessible by the light rays.

One version of an ultraviolet light sterilizer has been available in the market place from Despatch Industries, which device is designed to transport small plastic bags of pre-sterilized items into a clean room. This version, however, does not lend itself to production line use, and can only be used for batch preparation. Furthermore, the concentric design of the equipment does not allow for good sterilization of the ends of the packages, and the heat generated by the U. V. lights is sufficient to melt plastic wrap.

Accordingly, there exists a need in the industry for a device and method for surface sterilization of items to be introduced into a clean room without breaking sterility of the room, and particularly with regard to such items which have irregular surfaces and those which may have already been sterilized, but are enclosed in an exterior wrapping which is necessarily somewhat contaminated, if only by previous exposure to the ambient environment.

Thus, in view of the above, it is among the several goals of the invention to provide a device for sterilizing the surfaces of packages, which device can be used in a production line and which can be operated automatically for continuous pass-through sterilization of packages from a "dirty" (non-clean, or not class 100" side of the device, sometimes referred to as a dirty room or area, to a clean area or room.

It is further among the goals of the present invention, having the features indicated, that the device be capable of completing a sterilization cycle in a brief period of time, such as approximately one minute, and which can function appropriately with packages of various sizes and shapes. Ideally, the device can be manufactured in various sizes so that even greater flexibility on package size and production rates of sterile product can be realized.

It is still further among the several goals of the present invention, having the features indicated, that the device be capable of sterilizing items made of plastic with out creating so much heat that such items are caused to melt in the sterilization process, and that no health risks, such as burns (from steam, or ultraviolet light) and noxious or dangerous vapors exist to personnel using the device.

The present surface sterilizing device accomplishes the above goals by providing a combination of a pass-through tunnel for the goods to be sterilized and by including within one device both HEPA filtration as well as ultraviolet light at such high intensity that the cycle can be completed very quickly, yet without intense heat build-up.

In furtherance of the above objects, the present invention is, briefly, a device for surface sterilization of objects, the device including a housing having a first end and a second end and extending continuously therebetween, a conveyor assembly including a frame, a conveyor bed selectively movably connected to the frame, and a plurality of legs spacedly disposed beneath and supporting the frame above a support surface, at least part of the conveyor bed located longitudinally within the housing, to thereby movably support objects to be surface sterilized as they are passed from a contaminated area to a clean area, an air filtration system in communication with the housing, at least one ultraviolet light assembly located within of the housing and capable of providing ultraviolet irradiation of sufficient strength for a sufficient period of time to decontaminate the object to be surface sterilized within the sterilization device as the object to be sterilized is transferred via the conveyor through the housing and into the clean area, and controls by which an operator of the device can operate the conveyor, the air filtration system and the ultraviolet lights of the device.

The invention is also, briefly, the combination of a conveyor for passing objects to be sterilized from a contaminated area to a clean area, a housing over at least part of the conveyor, and an air filtration system mounted on and in communication with the housing, wherein the housing includes a portion having at least one ultraviolet light assembly, and further wherein the air filtration system includes a HEPA filter.

The invention is further, briefly, a method of sterilizing surfaces of objects to be passed from a non-sterile area to a sterile area, the method including placing an object which is to be surface sterilized on an intake end of a conveyor which passes through a housing connecting a contaminated area to a clean area, causing the conveyor to move through the housing toward the clean area, applying HEPA air filtration along at least a part of the length of the conveyor within the housing, exposing the object on the conveyor to ultraviolet light as it is carried on the conveyor through the housing, and passing the surface sterilized object on the conveyor through an output portion of the housing and into a clean room.

These and other objects and benefits of the invention are in part apparent and in part pointed out hereinbelow.

BRIEF DESCRIPTION OF THE DRAWINGS

FIG. 2 is vertical sectional view of the device of FIG. 1, taken on line 2—2.

FIG. 3 is vertical sectional view of the device of FIG. 1, taken on line 3—3 in FIG. 2.

FIG. 4 is schematic, perspective view of an ultraviolet light assembly of a type used in the device of FIG. 1, such as that shown in end elevational view in circled area number 4 in FIG. 3.

FIG. 5 is a schematic side elevational view of a roller if a type used in the device of FIG. 1.

FIG. 6 is a schematic, cut-away view of the attachment of the roller of FIG. 5, taken on line 6—6.

FIG. 7A. is a schematic perspective view of the device of FIG. 7, partially broken away, for clarity of the overall general structure.

FIG. 11 is a partial vertical sectional view taken on line 11—11 of FIG. 8.

FIG. 12 is a schematic, partially cut-away end view of the sterilizer device of FIG. 7.

Throughout the drawings like parts are indicated by like element numbers.

DESCRIPTION OF PRACTICAL EMBODIMENTS

Figure 1:
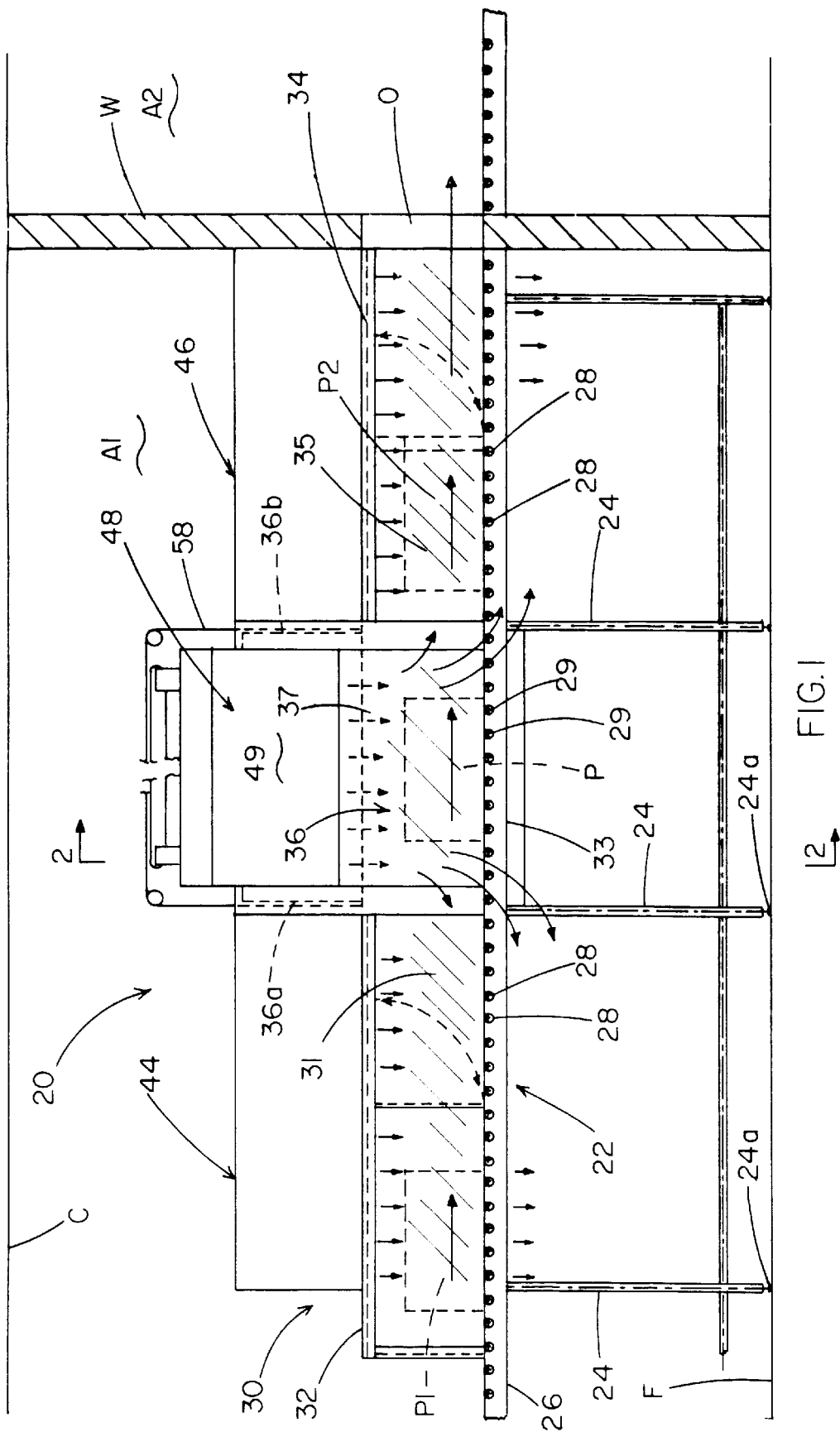
FIG. 1 is a schematic, side elevational view, partially broken away, of a sterilizing device constructed in accordance with the present invention.

With reference to the drawings, 20 (in FIGS. 1–6) and 200 (in FIGS. 7–13) generally designate alternative practical constructions of a surface sterilizer device constructed in accordance with and embodying the present invention. It should be understood that the new sterilizer will at least sometimes be manufactured on the basis of custom requirements, varying in some respects with the needs of the customer. However, all embodiments of the invention have in common a conveyor assembly which is supported above a surface, such as floor F, and which is covered by a housing for substantially the entire length of the conveyor assembly.

Also in common among the various new sterilizer device constructions, one end of the conveyor assembly meets (and can optionally in part pass through) an opening O in a wall W which separates a dirty area or room A1 from a clean room or area A2. Except for opening O, the perimeter of which is contiguously met on the A1 side by the sterilizer housing or conveyor as shown, wall W extends continuously from floor F to ceiling C, in order to provide a physical barrier and thereby partly enable maintenance of sterile conditions in clean room A2.

In each embodiment of the invention, within or in communication with the conveyor housing there is provided an air filtration system and at least one ultraviolet light assembly, which are both described in more detail hereafter with reference to specific practical embodiments. It is to be understood that the embodiments described in detail hereafter are merely examples of the invention. Although capable of being standardized for mass production, it is more likely that the new sterilizer device will usually be manufactured in a customized manner, to suit the particular space limitations and product sterilization requirements of the customer/user.

Referring now to the first practical embodiment, as illustrated in FIGS. 1 through 6, 20 generally designates a surface sterilizer device including a conveyor assembly 22 supported above floor F or other support surface by a plurality of legs 24 which are spaced apart and connected in known manner beneath conveyor 22 so as to securely and stably maintain conveyor 22 in its desired position for the above-discussed use. Legs 24 are of any number required and are reinforced by cross-bars and the like, as however may be necessary to provide as useful amount of strength and stability to device 20. Adjustable legs supports 24a or other leg adjustment means of any known variety are ordinarily provided as part of legs 24, in order that sterilizer device 20 can be selectively positioned for use, to accommodate the comfort of a particular user loading the conveyor, or, for example, the height of opening O in wall W. Of course legs 24 could be of a fixed length if the user is confident of the precise height needed for the sterilizer and conveyor assembly thereof.

Conveyor assembly 22, may be of various known constructions, for example, a known type of conveyor referred to as the "walking beam" variety may be desired for certain uses. However, conveyor assembly 22 is more often preferably of the indexing roller type known as a "line shaft live roller conveyor". One example of this type of conveyor is presently available from Automated Conveyor Systems, Inc. ("ACSI") and referred to in that company's Catalog #1190 as the Model "190-LS". This particular conveyor includes a generally elongated "bed" or frame 26 having two parallel side members ordinarily secured substantially horizontally to upwardly directed ends of legs 24. Although usually linear, it should be understood that conveyor assembly 22, and thus, sterilizer device 20, may conceivably be of a different overall shape, such as angled (by use of multiple linear sections), or even broadly curved, if necessary to suit requirements imposed by the environment in which device 20 is utilized.

A plurality of spaced-apart rollers 28, 29 are rotatably disposed within frame 26 in the usual manner, transversely in relation to the longitudinal axis of frame 26. Rollers 28 are those which are disposed beneath the intake module 32 and the output module 34 of housing 30. Rollers 29 are those disposed directly beneath the sterilization chamber or module 36.

Rollers 28 are preferably formed of aluminum, as usual, or other commonly used substances, such as certain plastics, which are desired to be economical, but of course must be of sufficient strength and durability to withstand the necessary weights and long periods of constant usage which may be required. Certainly, new materials, not yet developed, may be just as suitable for the required function.

Preferably those rollers 29 located under the sterilizing chamber 36 of device 20 are made of fused quartz tubing, in order to enhance reflection of the sterilizing U.V. light rays and to thereby reduce "shadows", i.e. areas not receiving full exposure, causing risk of incomplete sterilization. An example of one type of such fused quartz tubing is presently available from Technical Glass Products, Inc. of Mentor, Ohio, and is marketed under their registered trademark, SUPRASIL. Especially with the use of fused quartz rollers, and particularly if reflection means are included, it is possible that one such U.V. light assembly could be sufficient for sterilization purposes. However, for optimal exposure of package P to sterilizing light rays it is preferred that more than one such U.V. light assembly be incorporated into device 20. Such quartz tubing can be obtained from companies which specialize in glass products for technical applications.

As discussed further herein, rollers 28, 29 are preferably connected to frame 26 in known manner and caused to turn by known structure, such as by short circular drive belts, or O-rings, connected to a roller drive shaft which is in turn powered by a motor reducer drive. A small electric or other motor (not shown) of known type is conveniently mounted beneath frame 26, but can be positioned elsewhere.

The "tread" rollers 28, 29 of conveyor assembly 22 may be rotatably connected to frame 26 and used "as is" in commercially available conveyors. However, the ideal spacing between adjacent rollers (measured from the central longitudinal axes of the rollers) is at least approximately three inches, when the rollers used are about 1.9 to 2.0 inches in diameter. However, depending upon the intended us for device 20, the conveyor rollers 28, 29 may be somewhat larger or smaller in diameter and may be as much as at least five inches apart. The length of rollers 28, 29 will be as wide as is necessary to span the width of conveyor frame 26. In this embodiment, for example, rollers 28, 29 are each approximately 22 inches long.

Although amenable to some variation, the spacing and size of rollers 28, 29 is important, not only with respect to speed of travel of a package through housing 30, but also because if the package to be sterilized has an irregular configuration or is loosely wrapped, such as items in a large plastic bag, portions of the package may slip between adjacent rollers 28 and catch, causing jamming of the conveyor and stopping or slowing the sterilizing operation.

Rollers 28 are preferably capable of being selectively caused to rotate by conventional motor and control devices at such a rate that a package on conveyor assembly 22 travels at a speed in the range of at least 20 to approximately 200 linear feet per minute, with 100 to 150 feet per minute most likely being the most usable range. In combination with the other features of the invention, to be described hereafter, the preferred roller 28 configuration and speed provides for optimal package travel through sterilizer 20 and surface sterilization therein.

In some embodiments rollers 28 located at the input and output ends of conveyor assembly 22 may turn at different speeds from each other and from the speed of the rollers in the sterilization chamber portion 36, to be described further hereafter. This feature, which is readily managed by known conveyor technology, permits adaptation of the system to account for differences in rates of loading, unloading, and time required for sufficient exposure to the U.V. lights for maximum sterilization to occur.

As shown in FIGS. 2 and 3, rollers 28 are disposed substantially horizontally and transversely relative to the longitudinal axis of conveyor assembly 22. FIGS. 5 and 6 illustrate that rollers 28 are rotatably connected to frame 26, for example, by aluminum end caps or bushings 27 that are fixed to the opposed ends of rollers 28, desirably by a known and commercially available glue or adhesive (sometimes referred to as electrical adhesive) that is cured by brief exposure to ultraviolet light.

Roller shafts 27a extend centrally, outwardly and linearly from each bushing 27 and are journalled in appropriately spaced-apart openings or notches 25 in the parallel side rails of frame 26 (FIG. 6). At least one roller shaft 27a extending from each roller 26 connects to and is turned by rotation of a sprocket 27b (FIG. 5) which is caused to rotate in known manner and according to the speed preselected by the user for conveyor assembly 22.

Further detail regarding the known structure and operation of conveyor assembly 22 is omitted here for brevity and because literature on the conventional portions of the conveyor is readily available. Although the conventional line shaft structure and operation of conveyor assembly 22 as described herein is preferred, certainly modifications are conceivable which will function as well.

Supported above conveyor assembly 22, preferably by mounting on frame 26 is a housing assembly, generally designated 30, having a first open end for contaminated package input in dirty area A1, and a second open end which intersects wall W, on the A1 side, around opening O for output of sterilized packages. Housing 30 is preferably open-bottomed and usually has at least three sections, including an intake portion 32, an output portion 34.

A sterilization chamber 36 is connected to and is positioned between portions 32, 34 so that housing 30 is substantially contiguous with conveyor frame 26 along its entire length. However, the two extreme ends of frame 26 and the aluminum tread rollers 28 rotatably and transversely disposed at those ends will commonly, but not necessarily, extend somewhat beyond the ends of housing 30, as shown in FIG. 1, so as to facilitate input of non-sterile packages such as that indicated in FIG. 1 as P1 and output of sterile packages, such as that shown at P2.

In this first embodiment of the new sterilizer it is intended that intake module 32 of housing 30 have dimensions of approximately: four feet long, two feet wide and two feet high. Substantially the same dimensions are preferred for discharge module 34, and the sterilization chamber or U.V. module is approximately two feet high, two feet wide and two feet, six inches long. Of course, any of these dimensions can be varied as may be necessary for the proposed use.

As illustrated in FIG. 1, at least some of the side walls of housing 30 are formed of plexiglass or polycarbonate, as indicated at 31 and 35, at the sides of the intake and output modules, respectively, and having a thickness which permits ready observation of operation of the conveyor and sterilizing processes inside housing 30, but which is thick enough to simultaneously shield the user from unintentional exposure to ultraviolet irradiation which may by chance leak from the sterilization chamber during loading or unloading thereof.

The walls of housing 30 can certainly also be formed entirely, or in part, of stainless steel or other non-corrosive, highly durable substance. Although plexiglass certainly provides some shielding, it is preferred, because of the well known safety risks associated with ultraviolet light exposure, that the side walls 37 of sterilization chamber 36 be formed of stainless steel or some other metal to be absolutely sure of no transmission of ultraviolet light to the use environment.

If desired, some areas of the side walls of housing 30 can also include insulation, for example, as indicated at 33 in FIG. 2. If used, the insulation is preferably approximately 1 inch thick, depending upon the particular insulating substance chosen, but in any event is thick enough to minimize escape of heat from sterilizer chamber 36 into the ambient area. The walls of housing 30 can also be solid, at least in part, as indicated in FIG. 1 for portion 32, if access to the conveyor and housing interior is readily available via the nearest end opening of the housing.

Within sterilization chamber 36 there are mounted a plurality of ultraviolet light assemblies, such as those indicated, for example at 38 in FIGS. 2–4. U.V. light assemblies 38 typically include a bulb or medium pressure lamp 40 attached to the inner surface of a shield or reflector 42. Although a variety of constructions are feasible for light assemblies 38, in this embodiment of the new sterilizer device it is preferred that each assembly include a polished aluminum shield or reflector 42, such as that shown in FIG. 4 for example, and at least one U.V. bulb 40 connected to the inner surface of a corresponding reflector. ordinarily reflectors 42 are parabolic or substantially "V"-shaped in transverse cross-section, in order to maximize light reflection within chamber 36 and thereby ensure sterilization of all exterior surfaces of package P (or other object being sterilized). However, any shield shape providing a generally concave inner surface will such light reflection. Other materials are also potentially useful for forming reflectors 42.

In sterilizer 20 there are preferably 16 separate 100 watt per inch U.V. lamps 40, the majority of which are each attached to an individual corresponding reflector 42, for a total of 1600 watts. However, more than one bulb 40 could conceivably be attached to the same reflector, which reflector could be adapted in size and shape as desired or necessary to accommodate the multiple bulbs. Of course wattage of the U.V. lamps used may also vary, for example if exposure time is varied appropriately to obtain the necessary microorganism kill level. To avoid package melting during the sterilizing process, excessive heat from the lamps, if any, is overcome by selectively strobing the lamps, as well as by the additional cooling effect of the air forced through the sterilization chamber by the filtration unit above the chamber.

FIGS. 2 and 3 illustrate the desired, spaced-apart, placement of ultraviolet light assemblies 38. A total of 16 U.V. lamps 40 are used, with three on the sterilizer module ceiling, three within the plenum beneath quartz rollers 29, three on each of the facing inside side walls, and two on each of two doors (described further later herein), slideably mounted (for example as on tracks) at each end of sterilization chamber 36. Some reflectors 42 are omitted from the figures, for simplicity and clarity of the drawings.

As shown in FIG. 3, the U.V. lamps 40 within plenum 33 are spacedly disposed, parallel to each other in a plane beneath and parallel to the plane in which rollers 29 of chamber 36 are positioned. If desired, more or fewer U.V. lamp assemblies 38 can be used, and the placement and power thereof can be varied as necessary to provide adequate sterilization of package P within sterilization chamber 36. For example, a greater number of weaker U.V. bulbs can be used, and they can be positioned in plenum 33 between every two adjacent rollers 29 (but on a plane beneath the plane of the rollers 29), rather than between only three such pairs of rollers, as illustrated.

Moreover, the speed of conveyor assembly 22 can be adjusted as necessary, depending in part on the wattage of U.V. lights 40 used, to provide for adequate time of package P within chamber 36 so that a sufficient level of microbe kill can occur. A cost/benefit analysis must necessarily be performed for each use situation so as to account for desired output schedule and the costs inherent in increasing wattage and/or number of U.V. lights and speed of package pass-through.

The new sterilizer device 20 includes an air filtration system which provides the dual function of eliminating particulate matter and microscopic contaminants from the sterilization area, as well as providing a cooling effect, to reduce the effect of heat necessarily generated by the use of ultraviolet lights for sterilization.

Generally, the air filtration system is composed of a number of filtration modules disposed above conveyor housing 30 to force filtered air substantially vertically downwardly over and between the conveyor rollers 28, as indicated by the vertically disposed arrows in FIGS. 1–3. Note that as the housing over conveyor 30 is in part open-bottomed, the air which enters plenum 33 (beneath chamber 36), or any other area of housing 30 which optionally includes a bottom portion, the pressurized air will be forced along (and substantially parallel to) the underside of conveyor assembly 22 until exiting downwardly at a point (shown here at each end of conveyor assembly 22.

More specifically, the air filtration system of the new sterilizer device includes filtration of the well-known HEPA type and provides air quality of a purity level known in the industry as "Class 100". The preferred air filtration system is known as a low profile, fan powered system and is capable of moving air volume up to about 960 cfm with air flow at about 90 fpm. Such specifications are met by commercially available HEPA filter modules.

Steel housings of such known conveyors and the usual necessary motor/blower components (not shown) are necessarily quite heavy, so it is to be understood that device 20, and in particular conveyor assembly 30 is sufficiently strong and stable to safely and reliably support the air filtration system.

FIGS. 1–3 illustrate the preferred arrangement of filters and air filtration modules of the air filtration system conceived for this embodiment of the new surface sterilization device. FIG. 1 illustrates the exterior cabinet of a self-contained HEPA filtration module 44, securely mounted above conveyor housing input portion 32. A similar self-contained HEPA filtration unit or module 46 is mounted above output portion 34 of the conveyor housing 30. Likewise, a third self-contained HEPA filtration unit 48 is mounted over the sterilization chamber portion 36 of conveyor housing 30, contiguously and between units 44 and 46.

It is important for proper functioning of the entire sterilizing device that the joints or lines of connection between adjacent sections of the conveyor housing, as well as between adjacent HEPA filtration modules or units be substantially air tight, in order to prevent introduction of air which may have bypassed the filters.

The HEPA filtration system is shown in more detail in FIGS. 2 and 3. It is to be understood, however, that such filtration technology is well known in the art and variations from the arrangement shown can be conceived that will function adequately. other than size and possible external attachments (to be described), each of the HEPA filtration modules 44, 46, 48 is substantially the same, structurally and functionally, and thus only central module 48 will be discussed further.

In the present embodiment it is preferred that a pre-filter 50 be disposed in the exterior housing 49, to eliminate relatively larger particulate matter from air drawn in through the top of housing 49, in the usual manner. disposed below prefilter 50 is a fan 52. A HEPA filter 54 is mounted substantially horizontally within housing 49 beneath fan 52 and effectively divides the open top of housing section 36, the sterilization chamber, from the HEPA filtration chamber 48 mounted thereabove.

So mounted, the HEPA filter performs the highest level of filtration, the final air filtration step, removing even microscopic particles from incoming air and passing such cleansed air at a high volume and speed over the conveyor within a corresponding housing section directly beneath the filter module, in this instance, over the quartz rollers within the sterilization chamber. Air filtered in the same manner also passes over the optionally aluminum rollers under conveyor housing sections 32 and 34 as well.

Central air filtration module 48 differs from attached, flanking modules 44 and 46 in this embodiment by having the additional features of commercially available cable cylinders 56 and pully-mounted cables 58 of known variety mounted in the manufacturer recommended or otherwise acceptable manner on a top surface of module 48. By operation of cables 58 with known manual or automatic control means, door 36a can be vertically slidably opened to permit entry of a package to be sterilized, and then closed, also in known manner, before operation of the U.V. lamp assemblies 38. After the sterilization cycle is complete, door 36b is opened, also by operation of cables 58, to permit exit of the surface sterilized package P on conveyor assembly 22.

Structures other than those shown for attachment and operation of doors 36a, 36b are certainly conceivable which will operate adequately, although they may not be as convenient as the preferred structure just described. One acceptable alternative construction is described hereafter in detail with reference to the second embodiment of the invention.

With reference to the second practical embodiment illustrated in FIGS. 7–13, unless specified to the contrary, all constructions and alternatives discussed with reference to the first embodiment described with reference to FIGS. 1–6 also apply here, to this second described embodiment of the invention, as acceptable, useful constructions. The views in these figures are schematic in nature and some parts are omitted from some views, for simplicity and clarity of the drawings.

Figure 7:
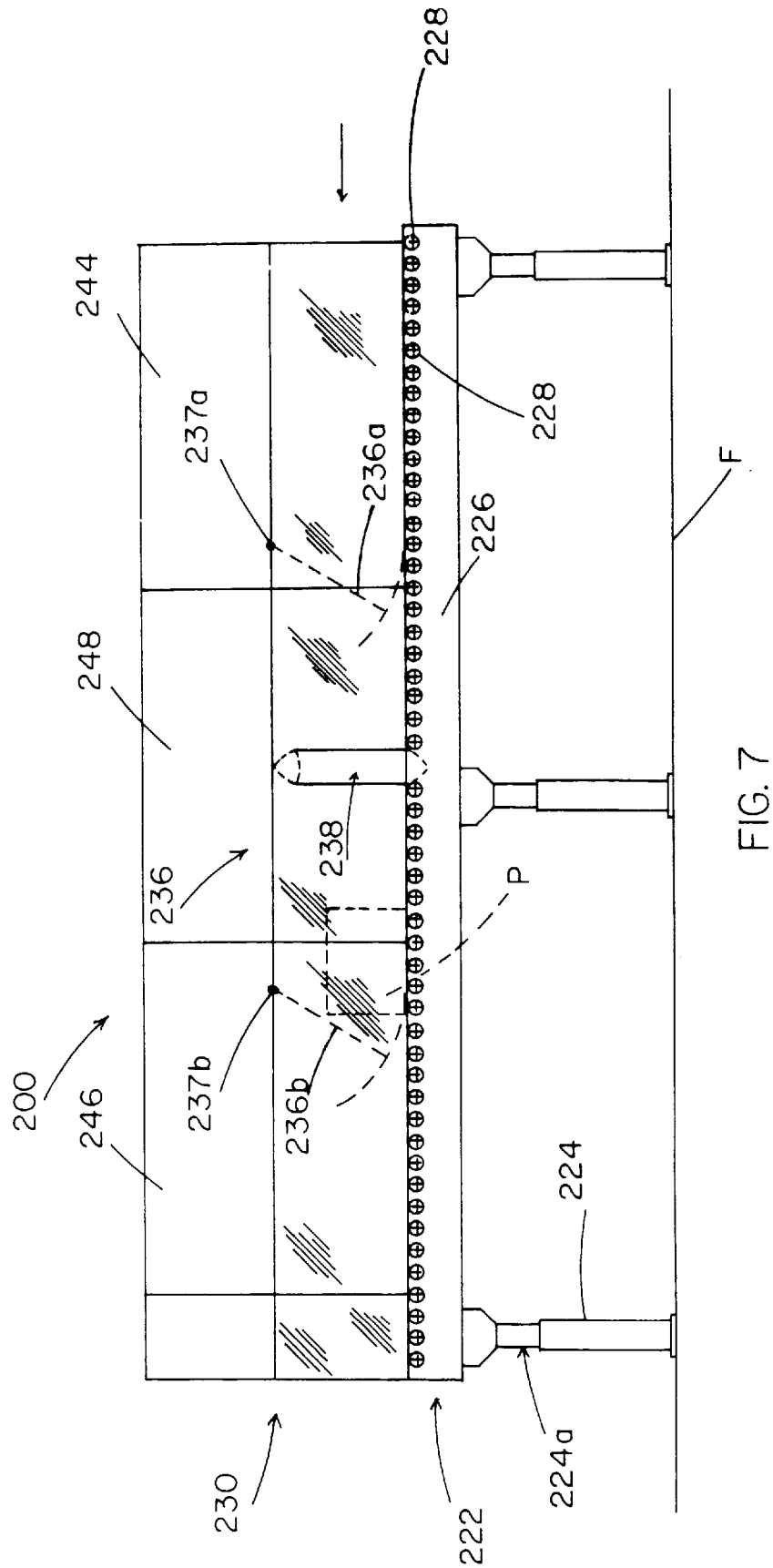
FIG. 7 is a schematic, side elevational view of another embodiment of the surface sterilizer device constructed in accordance with the present invention.
Figure 8:
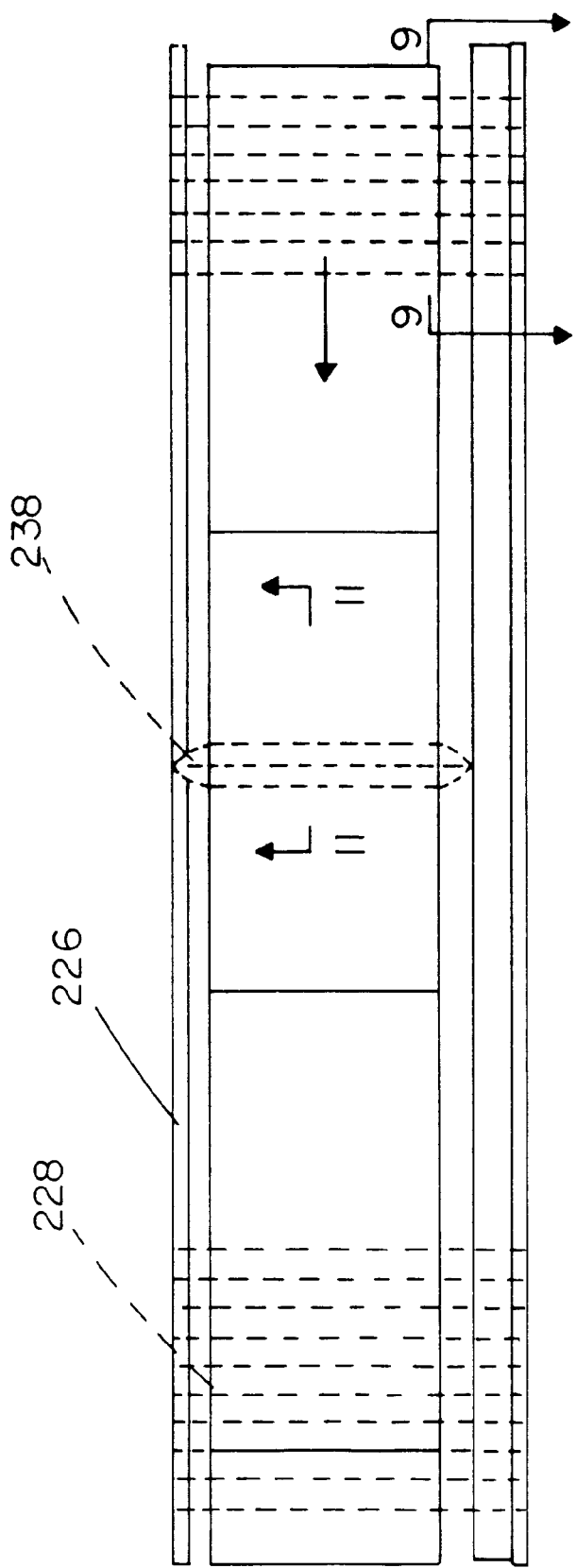
FIG. 8 is a top plan view of the device of FIG. 7.

It will be noted that in FIG. 7 device 200 is shown from the opposite side, as compared to device 20 in FIG. 1, and also as compared to the perspective view of device 200 in FIG. 7A. Thus, in FIG. 7 objects to be sterilized therein (not shown), will travel on the conveyor assembly 222 from the right to the left, as indicated by the arrow at the right side of the figure.

The structure of sterilizer device 200 is consistent with that of device 20 in that it includes a conveyor assembly 222 mounted on a plurality of spaced apart legs 224, which legs are preferably provided with some sort of adjustment mechanism, such as the telescoping structure indicated at 224a, for example.

Conveyor assembly 222 includes a frame 226 for a "bed" preferably having a plurality of selectively spaced apart transversely mounted selectively rotatable tread rollers 228, but, as in the previous embodiment, could conceivably have other means for causing an object to be sterilized to move through housing 230.

Conveyor assembly 222 is at least in part covered by a housing, generally designated 230. As in the first embodiment, housing 230 is effectively a series of interconnected housing units or modules which include intake and output modules and a sterilization chamber connected therebetween in a contiguous manner so that any seams or joints between adjoining housing modules is essentially airtight. However, conveyor assembly 222 and housing 230 are both substantially open-bottomed to permit passage of air outwardly and downwardly, as it is forced in like manner to device 20 by an air filtration system mounted above housing 230.

The air filtration units 244, 246, 248 which make up the air filtration system of device 200 are indicated only schematically in FIG. 7, as they are considered to be the same, with regard to arrangement of filters, fans, blowers, etc. as described with reference to device 20. All acceptable variations for one embodiment are expected to also be acceptable for the other embodiment. The key point in each case being that the filtration type will provide air quality meeting at least Class 100 standards and preferably including filters of the known type referred to as HEPA.

In both embodiments shown 20, 200, and other acceptable embodiments, it is preferred that the air filtration system cover substantially the entire length of the corresponding housing 30, 230 by being in communication with and mounted above the housing. Nonetheless, it is conceivable that some other acceptable constructions are possible in which the air filtration system may be, for example, side mounted and/or in communication with only a portion of the housing, the remaining housing portions being closed on the tops and sides.

Surface sterilizer device 200 is shown schematically in the side elevational view of FIG. 7 to vary most significantly from device 20 of the first embodiment in the particular elements of the doors leading in and out of the sterilizing chamber portion of the housing, and by the arrangement of U.V. light assemblies 238 within chamber 236 of housing 230.

Rather than the track-mounted, cable assisted doors of the first embodiment, device 20, the second embodiment of incorporates the use of doors 236a, 236b, indicated by dotted lines in FIG. 7, which are mounted at their top edges on hinges, indicated at 237a, 237b. Thus, as a package, such as that indicated at P, or one of other suitable size and shape, passes through housing 230 on conveyor 222, in the direction indicated, it necessarily strikes door 236a, and subsequently door 236b, and pushes the doors open and upwardly in an arc. As the package clears the bottom edge of the swinging door, the door freely swings back, downwardly into a normal, substantially vertical position. Necessarily, package P must be of sufficient weight and doors 236a, 236b must be sufficiently relatively light, and hinged to swing freely, so that the package can readily push the door open, rather than the door blocking the path of the package and causing a jam or back-up of objects to be sterilized on the conveyor.

Doors 236a, 236b, like at least portions of the walls of housing 230, are preferably formed of plexiglass. For the doors this is desirable for light-weightedness and U.V. shield. For the housing walls plexiglass may be desirable to permit viewing of the conveyor as well as for safety, by at least partial blocking of U.V. irradiation from the work environment. Nonetheless, as in the first embodiment, the walls of housing 230, and of the air filtration modules connected thereto may also be formed of stainless steel or other suitable materials, as long as they are sufficiently durable and economical when considered as part of the entire cost/benefit analysis.

Like the first embodiment, in sterilizer device 200 the conveyor can include a bed of rollers 228 for movement of an object through housing 230. The conveyor can be of a variety of styles but is particularly preferred to be of either the known styles referred to as walking beam style, or the line shaft live roller type.

As in the first embodiment, the rollers in device 200 may be entirely of aluminum or other materials, but it is preferred that the rollers in the conveyor portion directly beneath the sterilization chamber 238 of housing 230 be formed of fused quartz to improve reflection of sterilizing light rays within the chamber. For simplicity of the discussion hereafter, all rollers in this embodiment are assigned element number 228, but it is to be understood that the rollers may vary as described in the material of which they are formed.

Figure 10:
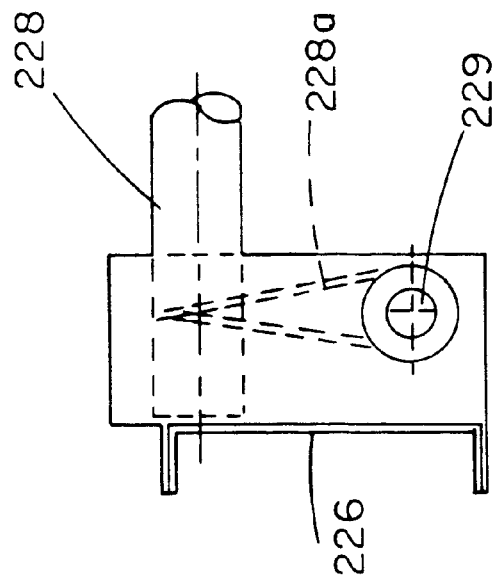
FIG. 10 is a partial sectional view taken on line 10—10 of FIG. 9.
Figure 9:
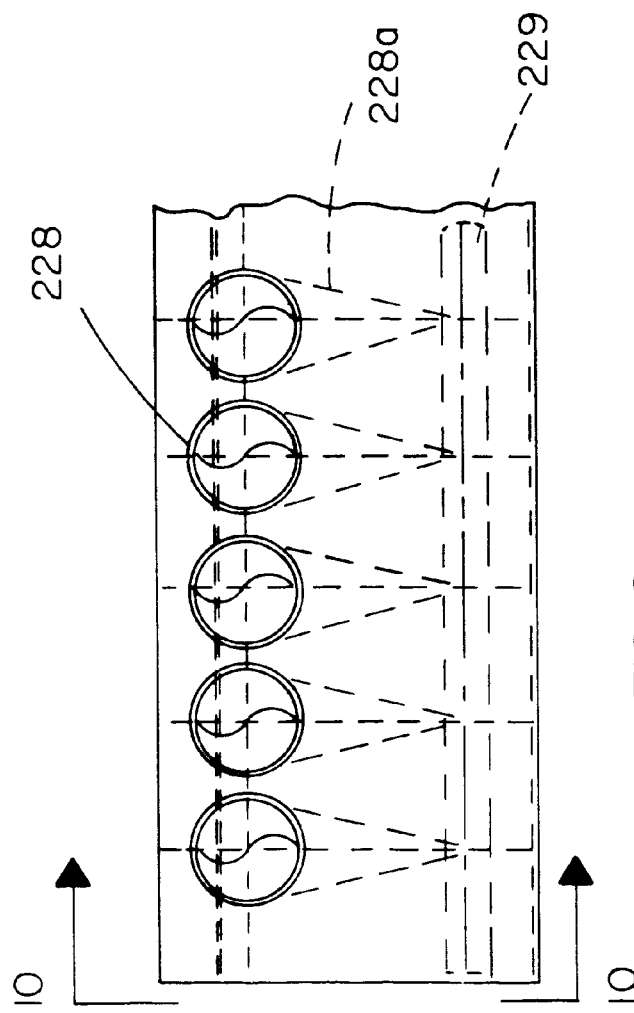
FIG. 9 is a partial vertical sectional view taken on line 9—9 of FIG. 8.

FIGS. 9, 10 and 12 illustrate the preferred arrangement of rollers 228 with the opposed ends thereof rotatably connected to frame 226, by known means (not shown), for example as described with reference to the first embodiment. Each roller 228 has a circular belt or "O"-ring 228a connecting one end of the roller to a drive shaft 229 which is rotatably mounted in known manner parallel to one side rail of conveyor frame 226. Drive shaft 229 is selectively caused to rotate, also in known manner, to effect rotation of rollers 228 at a preselected speed, which speed is controlled and varied depending upon the requirements of the particular use of device 200.

FIG. 12 also shows an acceptable mounting of the housing assembly on the frame 226 of the conveyor assembly 222. As shown, a flange 230a along the lower edge of the side wall of housing 230 can rest on the upper flange 227 or shoulder of the angle iron from which the side rails of conveyor frame 226 is preferably formed.

Flanges 230a and 227 can be connected by nut and bolt assemblies (not shown), welding, or any other appropriate and sufficiently strong known connectors. As is the case with the previous embodiment, other constructions for attaching housing assembly 30 to conveyor assembly 222 will suffice. Preferably, but not necessarily, this connection of parts is constructed so that the device 20, 200 can be disassembled, at least in part, for maintenance, cleaning and/or shipping.

FIGS. 7, 7A, 8, and 11–13 illustrate the arrangement and structure of the ultraviolet light assemblies 238 preferred for second preferred embodiment of the invention. A major difference between this embodiment and the first is that in sterilizer device 200 only four sterilizing light assemblies 238 are necessary. In contrast to sterilizer 20, no light assemblies are disposed upon doors 236a, 236b, so the swinging action of the doors and passage of a package thereby will not pose a hazard to the integrity of the lights. The assemblies 238 are generally situated as shown in FIG. 7A, with paired, opposed upper and lower substantially horizontally disposed, parallel assemblies, and paired, opposed substantially vertically disposed, parallel assemblies 238, so as to form a rectangular frame through which a package on conveyor assembly 222 will pass as it travels through the tunnel-like housing 230. The U.V. light assemblies 238 all face inwardly, toward the central longitudinal axis of the housing.

FIG. 11 shows such a package P approaching light assembly 238 within the sterilizing chamber portion of housing 230. Ultraviolet light rays 240a are indicated schematically to emanate from U.V. light lamp 240 and are reflected centrally toward the sterilization chamber by reflector shield 242. Reflector shields 242 are preferably parabolic in cross-section, with a U.V. bulb or lamp 240 longitudinally mounted on the concave surface of each shield 242. Indicated by the circles at the top and bottom of reflector shield 242 in FIG. 11 are two other bulbs 240, shown in cross-section.

In this embodiment it is preferred that U.V. bulbs 240 provide a total of 160,000 microwatts second/cm$^2$ of space and that they be on constantly when a package is in sterilization chamber 236. At this power level the heat produced by the four light assemblies 238 is not usually so great that heat will be produced to a level that melting of objects within chamber 236 is of concern. However, strobing of the ultraviolet lights in this embodiment can be employed in known manner. For example, strobing can be selectively applied if necessary for certain package or content materials which are particularly prone to melting and/or exposure times to avoid excess heat buildup. In each embodiment discussed and conceived herein, the ultraviolet lamps 40, 240 used are generally commercially available, and known in the industry. The wattage of U.V. light to which a package in the new device is exposed can be measured by a traveling U.V. meter in the customary manner.

Figure 13:
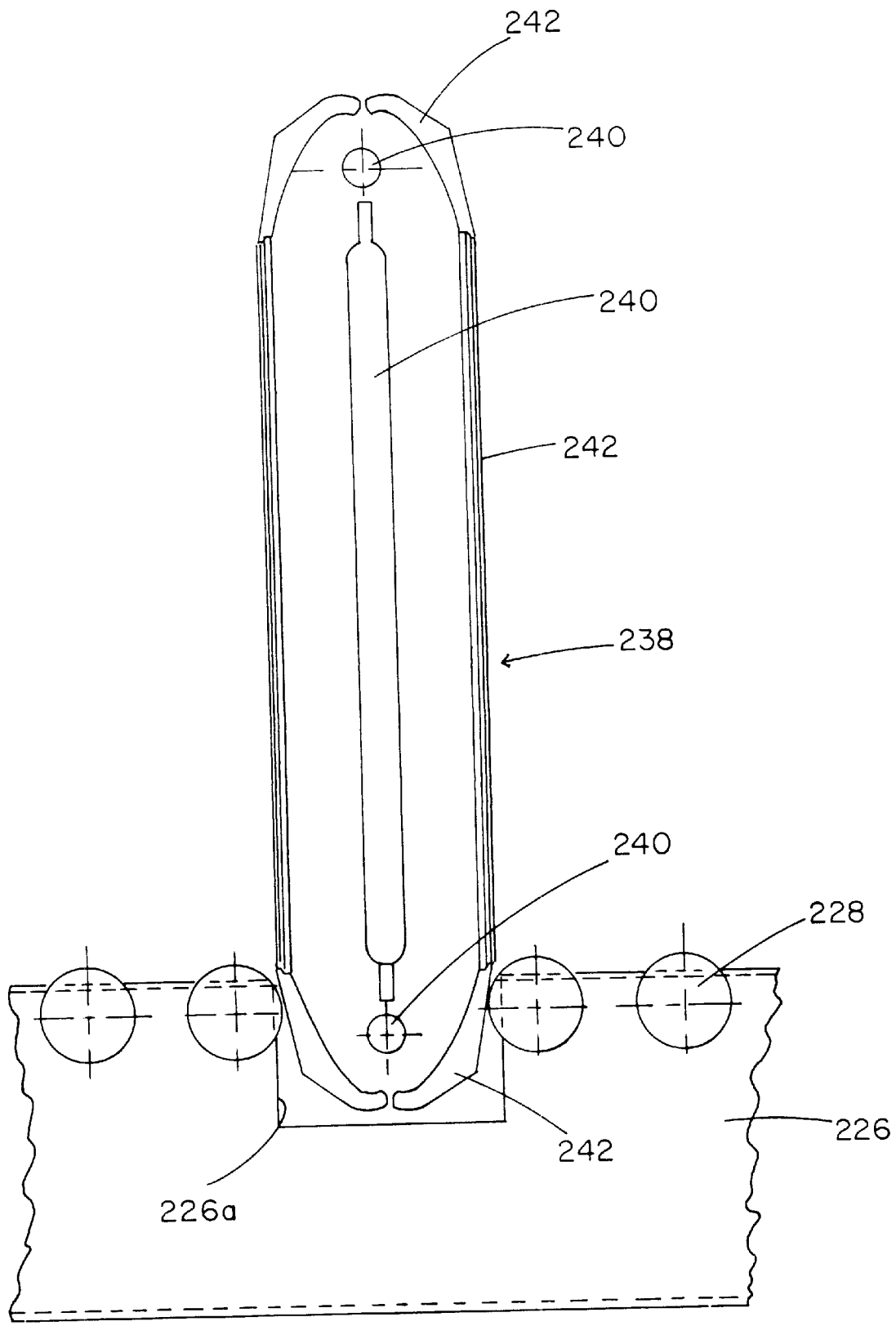
FIG. 13 is a partial, vertical sectional view taken on line 13—13 of FIG. 12, showing an ultraviolet light assembly enlarged for clarity.

FIGS. 11–13 illustrate that the lowermost horizontal ultraviolet light assembly 238 is disposed between two of rollers 228 in the conveyor bed. Although other mounting constructions may suffice, with this preferred arrangement light reflecting from rollers 228 in the sterilization chamber will not be blocked as much be the sides of the reflector shield 242 for the lowermost lamp 240 between the rollers as would be the case if the reflector shield side walls extended upwardly above the level of the rollers to any appreciable extent. If desired, a cutout area 226a may be formed in the side rails of conveyor frame 226 to accommodate the lower horizontal reflector shield 242, although other usual mounting arrangements are conceivable which may be as suitable.

FIG. 12 illustrates an acceptable mounting arrangement for the vertically disposed U.V. light assemblies 238 which are attached to the interior side walls of the sterilization chamber, for example by connecting shields 242 by brackets 241, welded or otherwise suitably attached to the walls and the shields. It is to be understood that the illustrated attachment is merely one example of an acceptable light assembly mounting arrangement. As with the first embodiment, other known mounting means for the light assemblies and well as various known constructions and attachment means for other portions of the new sterilizer device can be substituted satisfactorily. Furthermore, it will become apparent that various aspects of the two embodiments described may be substituted into the other embodiment, if necessary for a particular use application of the device.

As with device 20, in the second embodiment it is preferred that an object on the conveyor assembly will travel through the device, on average at a rate of 100 feet per minute, keeping in mind that different portions of the conveyor may operate in known manner, at different speeds. A range of about 20 to about 150 feet per minute travel on the conveyor is conceived, with a goal of processing approximately two packages per minutes being well within the realm of reason.

A still further possible variation on sterilizer device 20, 200 is conceived, wherein the ultraviolet light assembly includes at least one fiber optic element (not shown) having a quartz tip for emission of ultraviolet light rays, at least the quartz tip of the fiber optic element being insertable into an object on the conveyor (such as an open bottle, for example) when it is desired to sterilized the inner surfaces of the object. It is expected in such a case that the quartz tip of the fiber optic element preferably has a plurality of angled surfaces to increase the number of various directions in which the ultraviolet light rays passed from the quartz tip are reflected and thereby increase the coverage and decontaminating effectiveness of the ultraviolet light assembly.

As is clear from the above disclosure, the new surface sterilization device permits improved sterilization of packages having any type of surface structure, regular or irregular, and provides an automated method for so sterilizing package surfaces at an improved rate and with less health risk and reduced product damage, as compared to known structures and methods.

In view of the foregoing, it will be seen that the several objects of the invention are achieved and other advantages are attained.

Although the foregoing includes a description of the best mode contemplated for carrying out the invention, various modifications are contemplated.

As various modifications could be made in the constructions and methods herein described and illustrated without departing from the scope of the invention, it is intended that all matter contained in the foregoing description or shown in the accompanying drawings shall be interpreted as illustrative rather than limiting.

What is claimed is:

1. A device for surface sterilization of objects, the device comprising;
    a housing having a first end and a second end and extending continuously there between;
    a conveyor assembly including a frame, a conveyor bed selectively movably connected to the frame and a plurality of legs spacedly disposed beneath and supporting the frame above a support surface, at least part of the conveyor bed located longitudinally within the housing, to thereby movably support objects to be surface sterilized as they are passed from a contaminated area to a clean area;
    an air filtration system in communication with the housing;
    at least one ultraviolet light assembly located within the housing and capable of providing ultraviolet irradiation of sufficient strength for a sufficient period of time to decontaminate the object to be surface sterilized within the sterilizing device as the object to be sterilized is transferred via the conveyor through the housing and into the clean area; and
    controls by which an operator of the device can operate the conveyor, the air filtration system and the ultraviolet lights of the device;
    wherein the conveyor includes a plurality of rollers rotatably connected transversely along substantially the entire length of the conveyor, and further wherein at least the rollers of the conveyor which are positioned within the sterilization chamber are made of fused quartz, to thereby enhance reflection of U.V. rays within the sterilization chamber and increase contact of such U.V. rays with the surface of the object to be sterilized.

2. The device of claim 1, wherein the housing includes an intake portion disposed over the first end of the conveyor, an output portion disposed over the second end of the conveyor, and a sterilization chamber located between and in communication with the intake portion of the conveyor and the output portion of the housing and disposed over a substantially central portion of the conveyor.

3. The device of claim 2, wherein the at least one ultraviolet light assembly is attached to at least one inside wall of the sterilization chamber of the housing.

4. The device of claim 3, wherein the at least one ultraviolet light assembly comprises a plurality of ultraviolet light assemblies positioned spacedly about the interior walls of the sterilization chamber.

5. The device of claim 4, wherein the sterilization chamber includes a plurality of doors, and further comprising at least one ultraviolet light assembly attached to an interior surface of each of the doors of the sterilization chamber.

6. The device of claim 3, wherein the at least one ultraviolet light assembly includes an ultraviolet light bulb and a shield connected to the bulb and positioned to cause ultraviolet light rays from the ultraviolet light bulb to reflect toward the interior of the sterilization chamber, rather than outwardly and away from the interior.

7. The device of claim 1, wherein the air filtration system includes at least one air filtration module having a first filter which is a prefilter, and a second filter, and is capable of filtering out substances which range in size from that of particulate matter to that of microscopic contaminants such as bacteria and viruses, to prevent entrance of such contaminants into the housing.

8. The device of claim 7, wherein the air filtration system includes at least one air filtration module having a filter of the HEPA type.

9. The device of claim 8, wherein the at least one air filtration module comprises a first, a second and a third air filtration module, the first air filtration module being disposed above the intake portion of the housing, the second air filtration module being disposed above the output portion of the housing, and the third filter being disposed above the sterilizing chamber portion of the housing.

10. The device of claim 2, wherein at least one of the intake module, the output module and the sterilization chamber of the housing are open-topped, and connected to and in communication with an air filtration module of the air filtration system.

11. The device of claim 10, and further comprising a first door movably mounted between the intake module of the housing and the sterilization chamber and a second door movably mounted between the output module and the sterilization chamber, and means to effect opening and closing of the first door and the second door.

12. The device of claim 1, wherein the conveyor has more than one segment, and the rollers rotatably connected transversely along the extent of at least one portion of the conveyor are made of fused quartz, and further, the rollers rotatably connected transversely along the extent of at least one other portion of the conveyor are made of aluminum.

13. The device of claim 1, wherein the housing is open-bottomed, and has continuous side walls which extend entirely from the first end of the housing to the second end of the housing.

14. The device of claim 1, wherein the at least one ultraviolet light assembly is capable of providing a total of at least 1600 watts, to thereby assure an adequate bacterial kill rate when an object on the conveyor travels through the device at a rate in the range of approximately 20 to approximately 200 linear feet per minute.

15. The device of claim 1, wherein the at least one ultraviolet light assembly is capable of providing a total of at least 160,000 microwatts per second/$cm^2$, to thereby assure an adequate bacterial kill rate as an object on the conveyor travels through the device.

16. A device for surface sterilization of objects, the device comprising:

a housing having a first end and a second end and extending continuously there between;

a conveyor assembly including a frame, a conveyor bed selectively movably connected to the frame and a plurality of legs spacedly disposed beneath and supporting the frame above a support surface, at least part of the conveyor bed located longitudinally within the housing, to thereby movably support objects to be surface sterilized as they are passed from a contaminated area to a clean area;

an air filtration system in communication with the housing;

at least one ultraviolet light assembly located within the housing and capable of providing ultraviolet irradiation of sufficient strength for a sufficient period of time to decontaminate an object to be surface sterilized within the sterilization device as the object to be sterilized is transferred via the conveyor through the housing and into the clean area; and controls by which an operator of the device can operate the conveyor, the air filtration system and the ultraviolet lights of the device;

wherein the air filtration apparatus is capable of moving air at approximately 960 cfm and a force of approximately 90 fpm.

17. A device for surface sterilization of objects, the device comprising:

a housing having a first end and a second end and extending continuously there between;

a conveyor assembly including a frame, a conveyor bed selectively movably connected to the frame and a plurality of legs spacedly disposed beneath and supporting the frame above a support surface, at least part of the conveyor bed located longitudinally within the housing, to thereby movably support objects to be surface sterilized as they are passed from a contaminated area to a clean area;

an air filtration system in communication with the housing;

at least one ultraviolet light assembly located within the housing and capable of providing ultraviolet irradiation of sufficient strength for a sufficient period of time to decontaminate an object to be sterilized within the sterilization device as the object to be sterilized is transferred via the conveyor through the housing and into the clean area; and controls by which an operator of the device can operate the conveyor, the air filtration system and the ultraviolet lights of the device;

wherein the conveyor has more than one segment, each one of the more than one segment being capable of operating at a speed independent of the speed at which any other of the more than one segment is operating.

18. A device for surface sterilization of objects, the device comprising:

a housing having a first end and a second end and extending continuously there between;

a conveyor assembly including a frame, a conveyor bed selectively movably connected to the frame and a plurality of legs spacedly disposed beneath and supporting the frame above a support surface, at least part of the conveyor bed located longitudinally within the housing, to thereby movably support objects to be surface sterilized as they are passed from a contaminated area to a clean area;

an air filtration system in communication with the housing;

at least one ultraviolet light assembly located within the housing and capable of providing ultraviolet irradiation of sufficient strength for a sufficient period of time to decontaminate an object to be sterilized within the sterilization device as the object to be sterilized is transferred via the conveyor through the housing and into the clean area; and controls by which an operator of the device can operate the conveyor, the air filtration system and the ultraviolet lights of the device;

wherein the housing includes an intake portion disposed over the first end of the conveyor, an output portion disposed over the second end of the conveyor, and a sterilization chamber located between and in communication with the intake portion of the conveyor and the output portion of the housing and disposed over a substantially central portion of the conveyor;

wherein at least one of the intake module, the output module and the sterilization chamber of the housing are open-topped, and connected to and in communication with an air filtration module of the air filtration system; and further wherein all of the intake module, the output module and the sterilization chamber of the housing are open-topped, and the open-topped intake module of the housing is connected to and in communication with a first air filtration module of the air filtration system, the open-topped output module of the housing is connected to and in communication with a second air filtration module, and the open-topped sterilization chamber of the housing is connected to and in communication with a third air filtration module.

19. The device of claim 18, wherein the means to effect opening and closing of the first door and the second door comprises a cable and pulley system mounted on the third air filtration module and connected to the first door and the second door and wherein the first door and the second door are each mounted on tracks, to thereby permit slidable opening and closing upon operation of the cable and pulley system.

20. The device of claim 18, wherein the means to effect opening and closing of the first door and the second door comprises at least one hinge mounted at a top edge of the first door and at least one hinge mounted at a top edge of the second door, to thereby movably connect the first door and the second door between the intake module and the sterilization chamber and the output module and the sterilization chamber, respectively.

21. A device for surface sterilization of objects, the device comprising:
- a housing having a first end and a second end and extending continuously therebetween;
- a conveyor assembly including a frame, a conveyor bed selectively movably connected to the frame and a plurality of legs spacedly disposed beneath and supporting the frame above a support surface, at least part of the conveyor bed located longitudinally within the housing, to thereby movably support objects to be surface sterilized as they are passed from a contaminated area to a clean area;
- an air filtration system in communication with the housing;
- at least one ultraviolet light assembly located within the housing and capable of providing ultraviolet irradiation of sufficient strength for a sufficient period of time to decontaminate the object to be surface sterilized within the sterilization device as the object to be sterilized is transferred via the conveyor through the housing and into the clean area; and
- controls by which an operator of the device can operate the conveyor, the air filtration system and the ultraviolet lights of the device;
- wherein the housing includes an intake portion disposed over the first end of the conveyor, an output portion disposed over the second end of the conveyor, and a sterilization chamber located between and in communication with the intake portion of the conveyor and the output portion of the housing and disposed over a substantially central portion of the conveyor;
- wherein at least one of the intake module, the output module and the sterilization chamber of the housing are open-topped, and connected to and in communication with an air filtration module of the air filtration system;
- and further comprising a first door movably mounted between the intake module of the housing and the sterilization chamber and a second door movably mounted between the output module and the sterilization chamber, and means to effect opening and closing of the first door and the second door, wherein the means to effect opening and closing of the first door and the second door comprises a cable and pulley system mounted on the third air filtration module and connected to the first door and the second door and wherein the first door and the second door are each mounted on tracks to thereby permit slidable opening and closing upon operation of the cable and pulley system.

22. A device for surface sterilization of objects, the device comprising:
- a housing having a first end and a second end and extending continuously therebetween;
- a conveyor assembly including a frame, a conveyor bed selectively movably connected to the frame and a plurality of legs spacedly disposed beneath and supporting the frame above a support surface, at least part of the conveyor bed located longitudinally within the housing, to thereby movably support objects to be surface sterilized as they are passed from a contaminated area to a clean area;
- an air filtration system in communication with the housing;
- at least one ultraviolet light assembly located within the housing and capable of providing ultraviolet irradiation of sufficient strength for a sufficient period of time to decontaminate the object to be surface sterilized within the sterilization device as the object to be sterilized is transferred via the conveyor through the housing and into the clean area; and
- controls by which an operator of the device can operate the conveyor, the air filtration system and the ultraviolet lights of the device;
- wherein the housing includes an intake portion disposed over the first end of the conveyor, an output portion disposed over the second end of the conveyor, and a sterilization chamber located between and in communication with the intake portion of the conveyor and the output portion of the housing and disposed over a substantially central portion of the conveyor;
- wherein at least one of the intake module, the output module and the sterilization chamber of the housing are open-topped, and connected to and in communication with an air filtration module of the air filtration system;
- and further comprising a first door movably mounted between the intake module of the housing and the sterilization chamber and a second door movably mounted between the output module and the sterilization chamber, and means to effect opening and closing of the first door and the second door, wherein the means to effect opening and closing of the first door and the second door comprises at least one hinge mounted at a top edge of the first door and at least one hinge mounted at a top edge of the second door to thereby movably connect the first door and the second door between the intake module an the sterilization chamber and the output module and the sterilization chamber, respectively.

23. A method of sterilizing all exterior surfaces of objects to be passed from a non-sterile area to a sterile area regardless of the shape of the objects to be sterilized; the method comprising:
- placing an object which is to be surface sterilized on an intake end of a conveyor bed including a plurality of fused quartz rollers rotatably connected transversely along at least a portion of the length of the conveyor bed, which conveyor bed passes through a housing connecting a contaminated area to a clean area;
- causing the conveyor bed to move through the housing toward the clean area;
- applying HEPA air filtration along at least a part of the length of the conveyor bed within the housing;
- exposing all exterior surfaces of the object on the conveyor bed to a sufficient level of ultraviolet light as the object is carried on the conveyor bed through the housing to cause sterilization of all such exterior surfaces of the object; and passing the completely surface sterilized object on the conveyor bed through an output portion of the housing and into a clean room.

24. The method of claim 23, wherein the step of causing the conveyor to move is performed at a pass-through rate of at least two objects per minute.

25. The combination of a walking beam conveyor for passing objects to be completely surface sterilized from a contaminated area to a clean area, a housing over at least part of the walking beam conveyor, and an air filtration system mounted on and in communication with the housing, wherein the housing comprises a portion having at least one ultraviolet light assembly mounted internally of the housing to thereby sterilize all exterior surfaces of objects to be completely surface sterilized in the housing, and further wherein the air filtration system includes at least one HEPA filter, the air filtration system being capable of moving air at approximately 960 cfm and a force of approximately 90 fpm.

26. A device for surface sterilization of objects, the device comprising:

a housing having a first end and a second end and extending continuously therebetween;

a conveyor assembly including a frame, a conveyor bed selectively movably connected to the frame and a plurality of legs spacedly disposed beneath and supporting the frame above a support surface, at least part of the conveyor bed located longitudinally within the housing, to thereby movably support objects to be surface sterilized as they are passed from a contaminated area to a clean area;

an air filtration system in communication with the housing;

at least one ultraviolet light assembly located within the housing and capable of providing ultraviolet irradiation of sufficient strength for a sufficient period of time to decontaminate the object to be surface sterilized within the sterilization device as the object to be sterilized is transferred via the conveyor through the housing and into the clean area;

controls by which an operator of the device can operate the conveyor, the air filtration system and the ultraviolet lights of the device;

wherein the housing is open-bottomed, and has continuous side walls which extend entirely from the first end of the housing to the second end of the housing;

and further comprising a plenum connected beneath the conveyor frame, beneath the sterilizing chamber portion of the housing.

27. A device for surface sterilization of objects, the device comprising:

a housing having a first end and a second end and extending continuously therebetween;

a conveyor assembly including a frame, a conveyor bed selectively movably connected to the frame and a plurality of legs spacedly disposed beneath and supporting the frame above a support surface, at least part of the conveyor bed located longitudinally within the housing, to thereby movably support objects to be surface sterilized as they are passed from a contaminated area to a clean area;

an air filtration system in communication with the housing;

at least one ultraviolet light assembly located within the housing and capable of providing ultraviolet irradiation of sufficient strength for a sufficient period of time to decontaminate the object to be surface sterilized within the sterilization device as the object to be sterilized is transferred via the conveyor through the housing and into the clean area; and controls by which an operator of the device can operate the conveyor, the air filtration system and the ultraviolet lights of the device; wherein the at least one ultraviolet light assembly is capable of selective strobing to thereby prevent excessive heat buildup when the device is used for sterilization of objects which are prone to melting or which require extended exposure time periods for adequate sterilization.

28. A device for complete exterior surface sterilization of objects, the device comprising:

a housing having a first end and a second end and extending continuously therebetween;

a conveyor assembly including a frame, a conveyor bed selectively movably connected to the frame and a plurality of legs spacedly disposed beneath and supporting the frame above a support surface, at least part of the conveyor bed located longitudinally within the housing, to thereby movably support objects to be completely sterilized on all exterior surfaces of the objects, as the objects are passed from a contaminated area to a clean area, the conveyor bed including a plurality of rollers made of fused quartz connected transversely along at least a portion of the length of the conveyor bed within the housing, to thereby enhance reflection of U.V. rays within the housing and increase contact of such U.V. rays with the surface of the object to be sterilized;

at least one high intensity ultraviolet light assembly located within the housing and capable of providing ultraviolet irradiation of sufficient strength to decontaminate the exterior surfaces of an object to be sterilized within the sterilization device as the object to be sterilized is transferred rapidly via the conveyor through the housing and into the clean area;

an air filtration system in communication with the housing consisting essentially of at least one filter of the HEPA type, wherein the air filtration apparatus is capable of moving air through the device in sufficiently high volume and force to prevent buildup of heat from at least one high intensity ultraviolet light assembly, and controls by which an operator of the device can operate the conveyor, the air filtration system and the at least one high intensity ultraviolet light assembly of the device.

* * * * *